(12) United States Patent
Brandts

(10) Patent No.: US 8,981,136 B2
(45) Date of Patent: Mar. 17, 2015

(54) PROCESS FOR MAKING ESTERS

(71) Applicant: BASF Corporation, Florham Park, NJ (US)

(72) Inventor: Jim Aloysius Maria Brandts, De Meern (NL)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 14/350,688

(22) PCT Filed: Oct. 12, 2012

(86) PCT No.: PCT/IB2012/055556
§ 371 (c)(1),
(2) Date: Apr. 9, 2014

(87) PCT Pub. No.: WO2013/054306
PCT Pub. Date: Apr. 18, 2013

(65) Prior Publication Data
US 2014/0364637 A1 Dec. 11, 2014

(30) Foreign Application Priority Data
Oct. 13, 2011 (EP) .................................. 11185085

(51) Int. Cl.
*C11C 3/00* (2006.01)
*C07C 67/03* (2006.01)
(52) U.S. Cl.
CPC .................. *C07C 67/03* (2013.01)

USPC .............................................. 554/169
(58) Field of Classification Search
USPC .............................................. 554/169
See application file for complete search history.

(56) References Cited

U.S. PATENT DOCUMENTS 5,508,457 A * 4/1996 Bayense et al. ................ 554/169

OTHER PUBLICATIONS

Suppes G J et al: "Transesterification of soybean oil with zeolite and metal catalysts", Applied Catalysis A: General, vol. 257, No. 2, Jan. 20, 2004, pp. 213-223.*
Galen J. Suppes', Mohanprasau A. Dasari, Eric J. Doskocil, Pratik J. Mankidy, Michael J. Goff; "Transesterification of soybean oil with zeolite and metal catalysts"; .Applied Catalysts A: General 257(2004) 213 233.

* cited by examiner

*Primary Examiner* — Deborah D Carr
(74) *Attorney, Agent, or Firm* — Elizabeth Pietrowski

(57) ABSTRACT

The invention relates to a process for making esters, in particular biodiesel, using heterogeneous catalysts. The invention provides a process for making biodiesel, in particular FAME, which process is versatile and robust. The process of the invention can be carried out continuously, in particular in a fixed bed reactor or a slurry reactor and may be operated in a continuous fashion. In accordance with the invention, the transesterification reaction of triglycerides is carried out using a heterogeneous catalyst that comprises a Group 4 silicate and less than 3 wt. % Na in the presence of at least one acid compound.

13 Claims, 1 Drawing Sheet

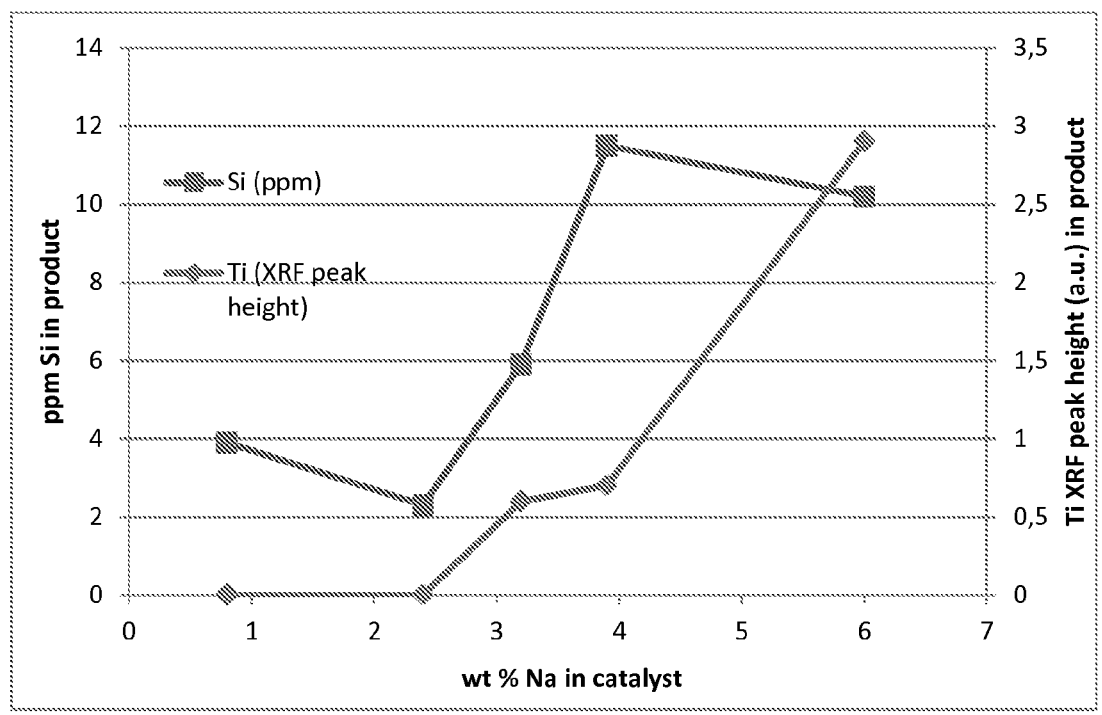

PROCESS FOR MAKING ESTERS

CROSS REFERENCE TO RELATED APPLICATIONS

This application claims priority from PCT/IB2012/055556 having a priority date of Oct. 12, 2012 based on EP 1118508.5, all of which are incorporated herein by reference in their entirety.

The present invention is directed to a process for making esters, in particular biodiesel, using heterogeneous catalysts.

The most common form of biodiesel comprises fatty acid methyl ester (FAME; $H_3COOR$). Biodiesel, in particular FAME is becoming more important as a fuel, in particular as transportation fuel.

In the prior art biodiesel has been produced in batch reactors in which oil (usually vegetable oil or sometimes animal fat), short-chain alcohols, in particular methanol and a homogeneous catalyst, such as NaOMe are combined and stirred at 50-80° C. at ambient pressures for 1 or 2 hours. The (trans-) esterification reaction produces FAME and glycerol:

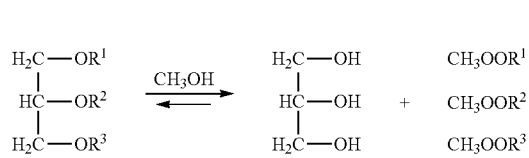

where $R^1$, $R^2$ and $R^3$ represent independently the long-chain part (typically C12-C20, more particularly C16-C18) of triglycerides or corresponding methyl esters, respectively.

In this known batch process the oil feedstock needs to be thoroughly pretreated, for instance by washing, steam treatment or vacuum to remove (free fatty) acids and water, as they may destroy the catalyst. Also, on the down stream side, the remains of the homogeneous catalyst need to be removed from the product, for instance by extensive washing.

Economically, it would be beneficial to employ heterogeneous catalysts since it facilitates separation of the reaction products and catalyst considerably when compared to homogeneous catalysts. Also heterogeneous catalysts can be used in slurry or fixed bed applications, which results in operational advantages in that inter alia high pressure drops can be avoided. Since separation of heterogeneous catalysts is much easier, the product can be much cleaner since no remains of (homogeneous) catalysts (e.g. the NaOMe mentioned above or other salts) or products derived from this, such as soaps or glycerol salts, have to be removed. Also the use of less corrosive catalysts and chemicals needed for up- and downstream purification, would imply less corrosion to the equipment. Furthermore this would ensure much safer operation. Also, by using a heterogeneous catalyst relatively high purity glycerol can be obtained.

Natural oils, including used oils, usually contain a certain amount of free fatty acid (FFA), typically ranging from 0.5 to 10 wt. % (some oils, such as rice bran oil may contain even up to 50 wt. %). In conventional methods for converting natural oils these free fatty acids need to be removed before contacting the feed with the homogeneous catalyst. This removal is typically done by the above-mentioned pretreatment procedures. Free fatty acids need to be removed in conventional methods to avoid high catalyst usage and/or the need to convert the FFA by esterification into the corresponding fatty acid methyl esters to meet the specifications (for instance DIN EN 14214). The esterification reaction proceeds as follows:

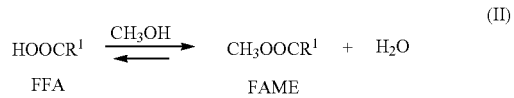

where $R^1$ has the same meaning as defined above. To convert free fatty acids in this esterification reaction it is important to use a catalyst that is highly stable. However, under the reaction conditions normally used many catalyst will dissolve in the presence of free fatty acids and the water that is formed, and the catalysts will therefore rapidly deactivate. Also (physical) degradation of the catalysts will occur, which may lead to unwanted fines formation and consequently unwanted pressure drops, in particular in fixed beds. Moreover, parts of the catalyst will end in the products that need to be removed to meet the specifications.

It is an object of the present invention to provide a process for making biodiesel, in particular FAME, which process is versatile and robust. A further object of the present invention is to provide such a process that can be carried out continuously, in particular in a fixed bed reactor or a slurry reactor and may be operated in a continuous fashion.

It was found these objects can be met at least in part by carrying out the transesterification reaction of triglycerides using a heterogeneous catalyst that comprises a Group 4 silicate and less than 3 wt. % Na, in the presence of at least one acid compound.

Surprisingly, it was found that in the presence of free fatty acid, Group 4 silicate comprising catalysts, in particular Ti, Zr and/or Hf silicate comprising catalysts, were more stable than under free fatty acid free conditions, when the catalyst is essentially free from, or very low in Na. Thus the present invention is directed to a process for producing esters, in particular biodiesel, more in particular FAME, which process comprises providing a feed of an oil and/or fat and an alcohol, in particular a short-chain alcohol, such as methanol, and contacting said feed with a heterogeneous catalyst, thus resulting in the transesterification of said oil and/or fat with said alcohol, characterized in that said heterogeneous catalyst comprises a Group 4 silicate and less than 3 wt. % Na, and said feed further comprises one or more acid compounds, in particular fatty acids.

Without wishing to be bound by theory, it is believed that the presence of an acid component in the feed mixture results in stabilization of the catalyst system used. Normally, viz. in the absence of acid compounds, the catalyst system would slowly degrade into titanium silicate particles (or the corresponding other Group 4 element/silicate particles) that are small enough to go through standard metal sintered filters or special micro filters (0.45 micron). The stability and/or solubility of these silicates, in particular titanosilicates is determined by the nature of the cations present in the catalyst. It is believed that titanosilicates containing for instance Na or K are much better soluble in the reaction mixture under the reaction conditions used. The presence of an acid, like for example a free fatty acid, makes it possible that a part of the cations are exchanged by protons ($H^+$). The protonated titanium silicates are less prone to degradate and dissolve in the feed or product stream. Replacing part of the cations (such as $Na^+$ or $K^+$) with H+ has also the advantage that the esterification activity of the catalyst increases. Typically the amount of Na or K ions is around 5-10 wt. % in fresh catalysts (i.e.

prior to contacting them with feedstock, in particular with (fatty) acids). In accordance with the present invention this sodium content is lowered by exchanging with $H^+$ to less than 3 wt. %. Preferably, in accordance with the present invention the potassium content is also lowered by exchanging with $H^+$ to less than 3 wt. %. More preferably the sodium or potassium content is lowered by exchanging with $H^+$ to less than 1 wt. %, even more preferably to around 0.1 to 0.2 wt. %. Instead of $H^+$ other cations may be used to exchange the Na or K ions, such $NH_4^+$, $Cs^+$ or $Ca^{2+}$.

The acid compound can be added to the feed stream or may already be present therein. Also it may be formed in situ from water that is either already present in the feed or added, since water will hydrolyze the ester bonds in the triglyceride and thus form the corresponding fatty acids. The acid may be organic acid or inorganic acid. Preferably the acid is a fatty acid. The amount of acid compounds in the feed may vary widely, for instance from 0.1 to 50 wt %, preferably it is from 1 to 30 wt. %.

The catalyst used in the present invention comprises at least one silicate of Group 4 of the Periodic Table, in particular a Ti, Zr and/or Hf silicate. Catalysts comprising titanosilicates are preferred. Titanium silicates for use in the present invention can be prepared by the procedures described in U.S. Pat. No. 5,508,457 and U.S. Pat. No. 5,053,139, both documents being incorporated herein by reference. Also the other silicates, in particular Hf and Zr silicates can be made using the procedures described in U.S. Pat. No. 5,508,457 and U.S. Pat. No. 5,053,139. Typically this involves creating a gel of silica and the Group 4 metal oxide, such as titanium oxide. This gel may be made by combining a suitable silicate source, e.g. sodium silicate, with a suitable soluble titanium (or other Group 4 metal) salt, such as the chloride, the bromide, the oxychloride, etc. and sufficient alkali with vigorous stirring. The gel is then dried, granulated and the resulting powder may be tabletted. These catalysts are able to perform both the esterification (Reaction II) and transesterification (Reaction I) reaction with alcohol. U.S. Pat. No. 5,508,457 does not describe ion exchanged titanium catalysts, having a reduced Na or K content, being used in the preparation of biodiesel.

Suppes et al. (Applied Catalysis A: General 257(2004)213-223) describes the transesterification of soybean oil with methanol in the presence of zeolites, such as titanium silicate ETS-10 zeolite and metal catalysts. Suppes et al. does not describe ion exchanged ETS-10 zeolites having a reduced Na content being used in the preparation of biodiesel.

The catalyst that may be used in the process of the present invention may further contain promoters, which are added to improve activity and/or selectivity. Suitable promoters are for instance cations such as Li, Cs, Mg, Ca, Sr, Ba, La, Nb, Fe, Ni, V, W, Mo, Al, Ce, Sn, Zn, Cu, Mn ions, or combinations thereof; anions such as $SO_4^{2-}$, $BF_4^-$, $CO_3^-$, $NO_3^-$, $PO_4^{3-}$, $F^-$, $Cl^-$, $Br^-$, $I^-$, $O^{2-}$, heteropoly acid anions, Keggin type anions or combinations thereof; and/or organic compounds, such as anionic organic compounds, e.g. $OR^-$, $RSO_3^-$, wherein R is an organic moiety; cationic organic compounds, e.g. ammonium, alkylammonium, arylammonium compounds; or neutral organic compounds, e.g. phosphines, amines, alcohols, or thiols; or combinations of these. The promoters are believed to change the electronic properties of the Group 4 metal site and thus may influence the catalysts activity and/or selectivity.

The present inventors found that only traces (much less than 0.1 wt. %) of titanium and silica were found in the product when free fatty acid was co-fed to the oil feedstock. Surprisingly, without free fatty acid, significant amounts of titanium and silicon were found in the product. The addition of some extra water to the feed had a similar effect on the stability of the catalyst. In the presence of water the catalyst showed higher stability.

The Group 4 silicate comprising catalysts can thus be used in accordance with the present invention for the simultaneous esterification and transesterification mentioned above.

The acid compound may either be co-fed or be already present in the feed (e.g. originating from the oil/fat or from the short-chain alcohol). Instead of, or in addition to an acid compound water may also be co-fed or be already present in the feed.

The alcohol is preferably an alcohol having 10 or less carbon atoms, more preferably it is a short-chain alcohol, preferably a short-chain alcohol selected from methanol, ethanol, iso-propanol, n-propanol, or combinations thereof. Preferably the alcohol is methanol. Long-chain alcohols (in particular larger than 10 C-atoms) are generally not preferred because it may result in the formation of waxes.

The present invention enables the production of a high purity FAME from oil in a continuous set-up without catalyst deactivation or catalyst degradation. The FAME can be free, or essentially free (less than 1 wt %), of salts, in particular of K or Na salts, because no homogeneous catalyst is used.

The glycerol that is produced is of high purity, in particular it may be as high as pharmaceutical grade (typically 98 wt. % pure) or even more. Because the process of the present invention does not require washing of the product to remove catalyst, the water content of the products, in particular of the glycerol is surprisingly low. In addition the Na and K content is also low, which is very desirable.

The triglyceride used as starting material in the present invention may be of any origin, in particular it may be from an oil and/or fat feed that is selected from soybean oil, rapeseed oil, palm oil, sunflower oil, safflower oil, jatropha oil, mustard oil, hemp oil, castor oil, waste vegetable oil, oil from microorganisms, algae oil, animal fat, trap grease and combinations thereof.

The invention will now be illustrated by the following examples, which are not intended to limit the scope.

EXAMPLE 1

10 mL titanium silicate tablets were made in accordance with the procedures of U.S. Pat. No. 5,053,139, in particular following Example 9 thereof: 2 dm$^3$ of a 1.5 M titanium chloride solution (solution A) was made by adding 569.11 g TiCl$_4$ to sufficient deionized water to make 2 dm$^3$. 2 dm$^3$ of 1.5 M sodium silicate solution (solution B) was made by dissolving 638.2 g of Na$_2$SiO$_{3.5}$.H$_2$O in sufficient 3M NaOH to make 2 dm$^3$. Solution B is added to solution A at a rate of 16 ml/minute with extremely vigorous stirring. After addition is complete, the mixture is allowed to continue mixing for an additional 15 minutes. The pH of the solution should fall between 7.5 and 7.9. If necessary, the pH was adjusted with dilute HCl or dilute NaOH. The sample was then allowed to age 2-4 days. After aging, any water on top of the gel was decanted off. The sample was then filtered, washed with 1 dm$^3$ deionized water per dm$^3$ of gel, reslurried in 4-6 dm$^3$ of deionized water, filtered, and finally rewashed in 2 dm$^3$ of water per liter of gel. The sample was then dried at 105° C. for 24 hours (until LOI (loss on ignition) was below 10). At no time during the synthesis procedure was the gel allowed to contact any metal. Polypropylene and glass labware were used throughout the preparation. The solids produced from this method had a silicon-to-titanium ratio of 1:1 and a surface area of approximately 350 m$^2$/g.

The resulting dried material was granulated to below 40 mesh and was tabletted. The tablets were loaded in a fixed bed reactor. The reactor was continuously fed with MeOH (1.73 ml/h) and rapeseed oil (3.47 ml/h). Reaction conditions were 180° C., 28 bars, $N_2$ back pressure, LHSV rapeseed oil 0.347 $h^{-1}$ (3.47 ml/h), LHSV MeOH 0.173 $h^{-1}$ (1.73 ml/h). LHSV total=0.5 $h^{-1}$. After 168 hours on stream the rapeseed oil was replaced by rapeseed oil containing 5 wt % dodecanoic acid. After a total 304 hours on stream the reaction was stopped and the product stream and catalyst was analyzed. The product stream that was produced with the pure rapeseed oil contained significant amounts, several tens to several hundreds of ppm (w/w) of titanium and silicon as was found by XRF (X-Ray Fluorescence Spectrometry). The product stream that was produced with the rapeseed oil that contained 5 wt % dodecanoic acid, contained only traces (several or tens of ppms (w/w)) of titanium and silicon.

EXAMPLE 2

10 mL of titanium silicate tablets made in accordance with the procedures of U.S. Pat. No. 5,508,457 were loaded in a fixed bed reactor. The reactor was fed with MeOH (1.73 mL/h) and rapeseed oil containing 5 wt % dodecanoic acid (3.47 mL/h). After 284 hours on the stream at 180° C., the reaction was stopped and the product stream and catalyst was analyzed. The product stream contained only traces of titanium and silicon (several or tens of ppms (w/w)).

EXAMPLE 3

10 mL of titanium silicate tablets with varying amounts of Na were prepared by treating the tablets prepared according to Example 1 with different amounts of HCl in water. The final Na content of the tablets could be controlled by controlling the pH of the water phase. After 2 hours of HCl treatment, the tablets were thoroughly washed with demi-water and were dried in an oven at 110° C. overnight. This procedure allowed the production of titanium silicate tablets with a distinct Na content, i.e. 6.0, 3.9, 3.2, 2.4 and 0.8 wt %, respectively.

The treated and untreated tablets were tested in a fixed bed reactor under similar conditions as described in Example 2. FIG. 1 shows the relationship between the amount of Na in the catalyst (wt. %) vs the amount of Si (ppm) and the amount of Ti (XRF peak height) in the product stream (see FIG. 1, line with squares and line with diamonds, respectively). When the amount of titanium and silicium in the final product was measured by XRF (x-ray fluorescence), a correlation between the amount of Na in the catalyst and the amount of Ti and Si in the product stream was found. At levels below 3 wt. % Na, no Ti was found in the product stream and only low amounts (few ppm's) of Si. At levels higher than 3 wt. % Na, increasing amounts of Ti were found in the product stream and increasing amounts of Si. The amount of Ti in the samples was determined by comparing the Ti peak height in the XRF spectrum of the feed with the Ti peak height of the product. The amount of Si was determined by measuring the peak height of the Si as measured with XRF and calculating the amount of Si the product stream using a calibration curve (XRF peak height vs known Si concentration).

The invention claimed is:

1. Process for producing esters, in particular biodiesel, which process comprises providing a triglyceride feed and an alcohol, and contacting said feed with a heterogeneous catalyst, thus resulting in the transesterification of said triglyceride with said alcohol, characterized in that said heterogeneous catalyst comprises a Group 4 silicate and less than 3 wt. % Na, and said feed further comprises at least one acid compound.

2. Process according to claim 1, wherein said biodiesel is a FAME containing product.

3. Process according to claim 1, wherein said alcohol is a short-chain alcohol.

4. Process according to claim 1, wherein said acid compound is a fatty acid, water or both.

5. Process according to claim 1, wherein said Group 4 silicate comprising catalyst comprises a titanosilicate.

6. Process according to claim 1, wherein the content of said free fatty acids in said feed is from 0.1-99 wt. %, based on the total weight of the feed.

7. Process according to claim 1, wherein said contacting of said feed with said catalyst is carried out in a fixed bed reactor or a slurry reactor.

8. Process according to claim 1, wherein said contacting of said feed with said catalyst is carried out at a temperature of 40-300° C.

9. Process according to claim 1, wherein said triglyceride is from animal, vegetable or microorganismal origin, comprised in an oil and/or fat feed that is selected from soybean oil, rapeseed oil, palm oil, sunflower oil, safflower oil, jatropha oil, mustard oil, hemp oil, castor oil, waste vegetable oil, algae oil, animal fat, trap grease and combinations thereof.

10. Process according to claim 1, wherein said catalyst further comprises a promoter.

11. Process according to claim 10, wherein said promoter is selected from: cations, anions; and/or organic compounds; or combinations of these.

12. Process according to claim 11, wherein:
said cation promoter is selected from selected from Li, Cs, Mg, Ca, Sr, Ba, La, Nb, Fe, Ni, V, W, Mo, Al, Ce, Sn, Zn, Cu, Mn ions, and combinations thereof;
said anion promoter is selected from $SO_4^{2-}$, $BF_4^-$, $CO_3^-$, $NO_3^-$, $PO_4^{3-}$, $F^-$, $Cl^-$, $Br^-$, $I^-$, $O^{2-}$, heteropoly acid anions, Keggin type anions and combinations thereof; and/or
said organic promoter is selected from:
anionic organic compounds;
cationic organic compounds;
neutral organic compounds; and
combinations thereof.

13. Process according to claim 1, wherein said catalyst contains less than 3 wt. % K.

* * * * *